(12) United States Patent  
O'Brien

(10) Patent No.: US 6,168,436 B1
(45) Date of Patent: Jan. 2, 2001

(54) UNIVERSAL DENTAL IMPLANT ABUTMENT SYSTEM

(76) Inventor: Gary O'Brien, 909 Cavanaugh Rd., Glendale, CA (US) 91205

( * ) Notice: Under 35 U.S.C. 154(b), the term of this patent shall be extended for 0 days.

(21) Appl. No.: 08/877,916

(22) Filed: Jun. 18, 1997

(51) Int. Cl.[7] ............................................. A61C 8/00
(52) U.S. Cl. .................... 433/173; 433/172; 433/173; 433/174
(58) Field of Search ................... 433/172, 173, 433/174

(56) References Cited

U.S. PATENT DOCUMENTS

| | | | |
|---|---|---|---|
| 5,026,280 | * | 6/1991 | Durr et al. ................... 433/173 X |
| 5,125,840 | * | 6/1992 | Durr et al. ................... 433/173 |
| 5,135,395 | * | 8/1992 | Marlin ......................... 433/173 X |
| 5,376,004 | * | 12/1994 | Mena .......................... 433/173 |
| 5,476,382 | * | 12/1995 | Daftary ....................... 433/173 X |
| 5,695,335 | * | 12/1997 | Haas et al. ................... 433/173 |
| 5,782,918 | * | 7/1998 | Klardie et al. ............... 433/173 X |

* cited by examiner

Primary Examiner—Nicholas D. Lucchesi
(74) Attorney, Agent, or Firm—Koppel & Jacobs; Michael J. Ram

(57) ABSTRACT

A universal dental implant abutment system is provided which includes an abutment collar and a fixation screw. The abutment collar has a proximal end portion adapted for fixation to a dental prosthesis and a distal end portion adapted for coupling with an implant body. The fixation screw is disposed within a longitudinal bore of the abutment collar and has a threaded distal end for securement to the implant body. The fixation screw has a head portion formed on a proximal end thereof, the head portion having a longitudinally directed bore formed therein. The longitudinal bore of the head of the fixation screw is formed with two longitudinally spaced sections. One section has a non-circular cross-sectional contour adapted for receiving a driving tool therein. The other section has internal threads formed therein adapted for threaded engagement with a retention fastener of a prosthesis.

22 Claims, 6 Drawing Sheets

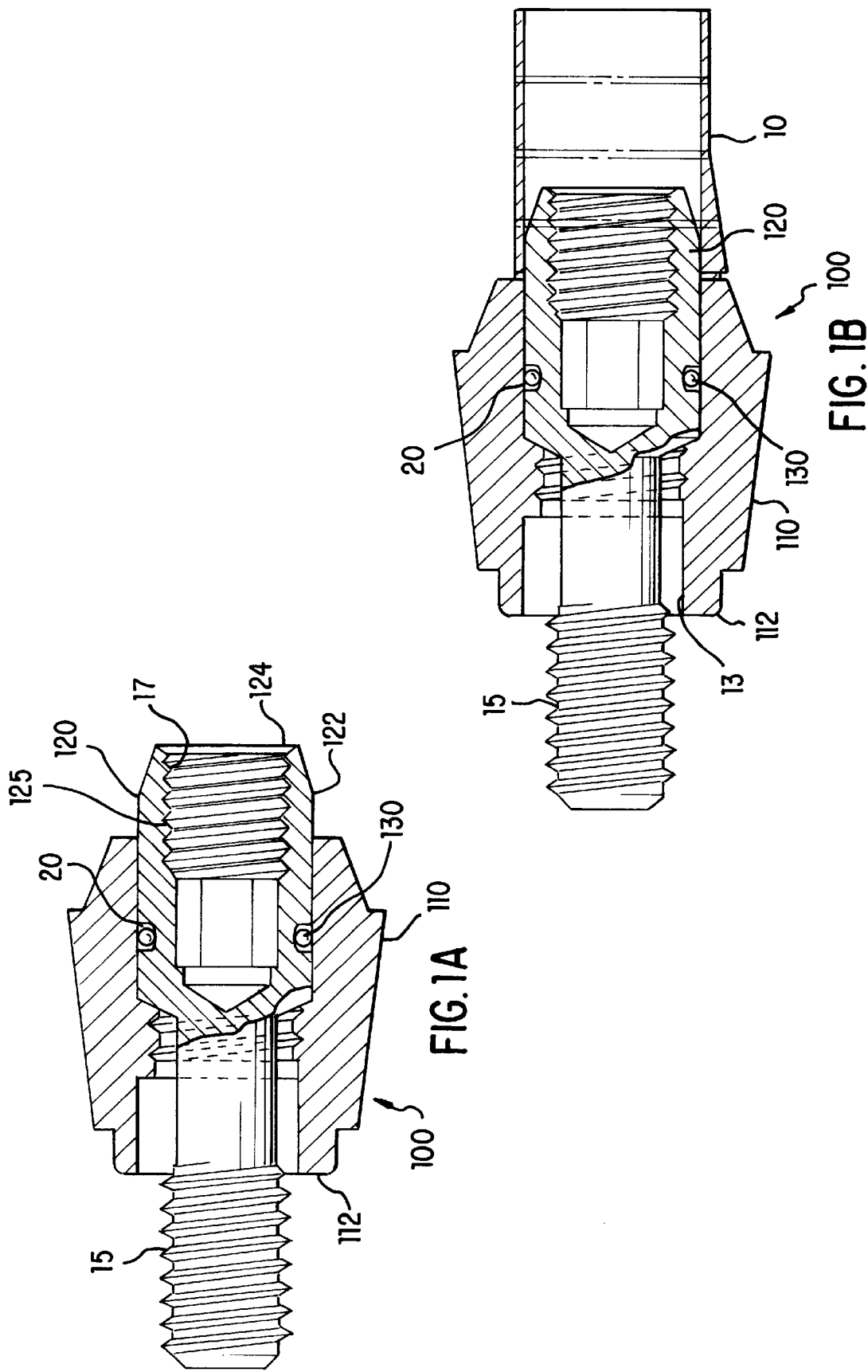

UNIVERSAL DENTAL IMPLANT ABUTMENT SYSTEM

BACKGROUND OF THE INVENTION

1. Field of the Invention

This invention is directed to dental implant devices. Particularly, this invention is directed to a universal dental implant abutment system comprising an abutment collar and a single fixation screw. Still further, this invention directs itself to a dental implant abutment system which is multi-functional in that the same elements may be utilized irrespective of the method by which the prosthesis is joined to the abutment collar. Still further, this invention directs itself to a fixation screw which is adapted to affix the abutment collar to a dental implant body, the fixation screw having a longitudinally directed bore having a first section of non-circular cross sectional contour adapted for receiving a driving tool therein. The longitudinally directed bore also includes a second section having internal threads formed therein adapted for threaded engagement with a retention fastener of a prosthesis.

2. Prior Art

Dental implant and prosthetic abutment systems are known in the art. Such systems are characterized by a threaded prosthetic coronal portion attached to a cylindrical or threaded implant root. In general, each of the known prior art dental implant systems require a vast array of threaded coronal prosthetic attachments to accommodate different restoration methods utilized in the dental practice. Currently, there are three primary restoration methods, a fixed single or multiple unit cementable crown prosthesis, a removable single or multiple unit screw retained prosthesis or a removable overdenture prosthesis. In order to accommodate these different restoration methods, a vast inventory of different components were needed, requiring a significant investment in time and money by dental professionals. That investment requirement thereby limiting the use of the implant technology and slowed its growth and development, the longstanding need for improved means for attaching dental implants efficiently became apparent.

To overcome these problems, the instant invention provides an abutment system formed by two components, an abutment collar and a fixation screw which are so constructed as to be used for all three primary methods of restoration. Through use of the instant invention, the manufacturer of dental implant systems is made more efficient, as fewer different components need be manufactured for use in restorations. The restoration itself is made more efficient as fewer components need be stocked by the practitioner, with the same components being utilized irrespective of the restoration method. Further, the instant invention provides a novel hybrid male/female connection with a dental implant body that improves the stability and rigidity of the connection between the abutment collar and the implant body.

SUMMARY OF THE INVENTION

A universal dental implant abutment system for securement to an implant body is provided. The universal dental implant abutment system includes an abutment collar having a bore extending longitudinally therethrough and a proximal end portion adapted for fixation to a dental prosthesis. The proximal end portion is removable for use with a prosthesis to be retained by a fastener. The universal dental implant abutment system also includes a fixation screw disposed within the longitudinal bore of the abutment collar and has a threaded distal end for coupling to an implant body. The fixation screw has a head portion formed on a proximal end thereof. The head portion has a longitudinally directed bore open on the proximal end and has first and second longitudinally spaced sections formed within the bore of the head portion. The first section has a non-circular cross-sectional contour adapted to receive a driving tool therein. The second section has internal threads formed therein adapted for threaded engagement with a retention fastener of a prosthesis.

It is an object of the invention to provide a single abutment system which can be utilized for restorations wherein the prosthesis is mounted to the abutment collar, or secured thereto by a fastener.

Another object of the invention is to provide an abutment that can be easily modified in a dental office or laboratory to provide for an instantaneous change in the restorative arrangement, without requiring any abutment.

A further object of the invention is to provide an abutment having a hybrid male/female anti-rotational connection with the implant body, such providing a rigid and stable connection.

Yet another object of the invention is to provide an anti-rotational tapered locking polygonal or keyway mechanism to the coronal aspect of the abutment collar to rigidly connect multiple unit screw retained prosthetics in only one position or multiple positions while minimizing the axial effect of draw.

Still another object of the invention is to provide a fixation screw having a cylindrical taper formed on a proximal end thereof which further aids in minimizing the prosthetic draw.

These and other advantages and novel features of the invention will become apparent in the following detailed description when considered in connection with the accompanying drawing Figures.

BRIEF DESCRIPTION OF THE DRAWINGS

FIG. 1A is an elevation view, partially sectioned, of the universal dental implant abutment system of the present invention with the coronal cylindrical chimney removed;

FIG. 1B is an elevation view, partially sectioned, of a universal dental implant abutment system with the coronal cylindrical chimney intact;

DESCRIPTION OF THE PREFERRED EMBODIMENT

Figure 1C:
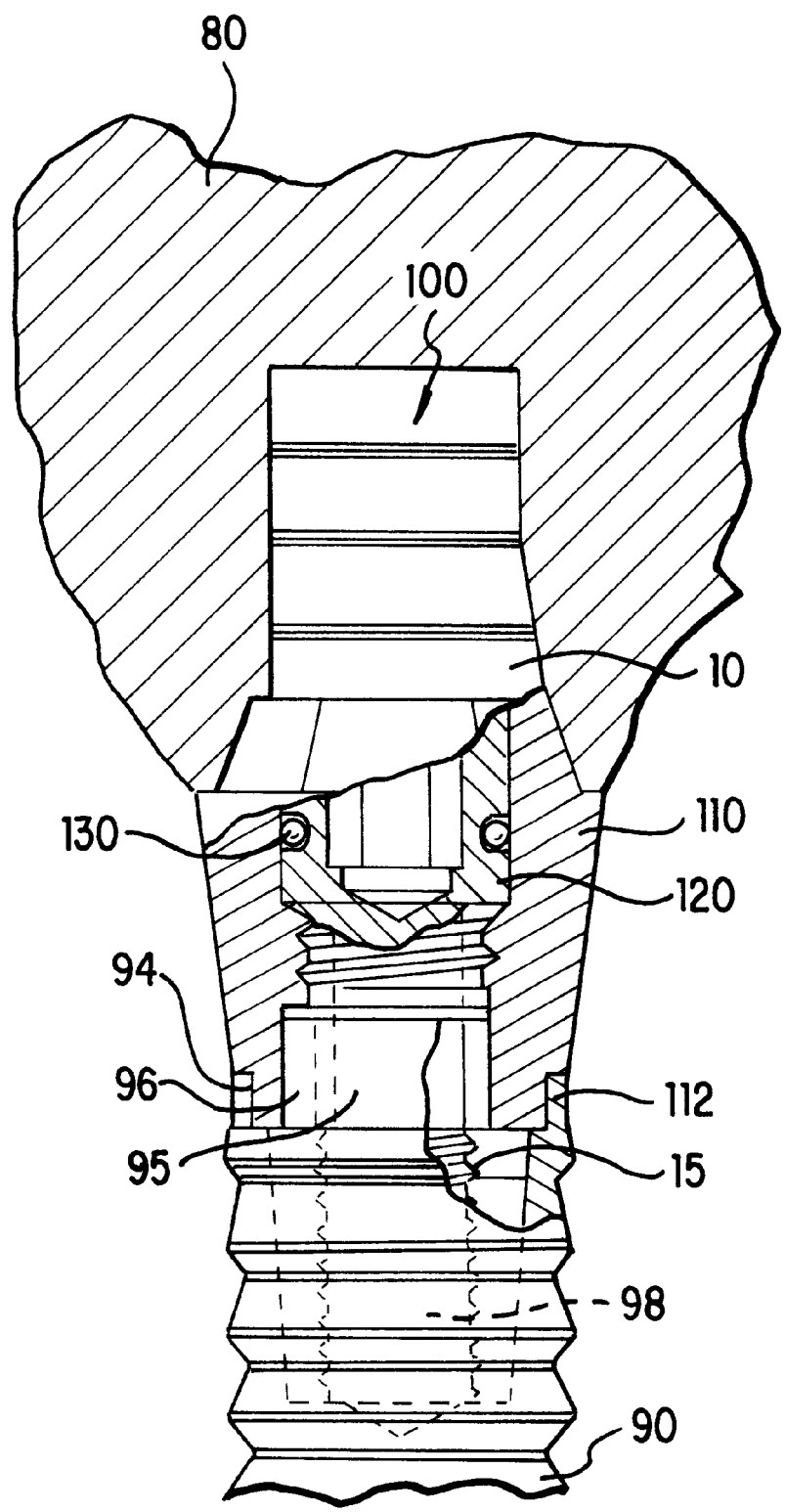
FIG. 1C is an elevation view, partially sectioned, of a universal dental implant abutment system coupled to an implant body and having a dental prosthesis secured thereto.

Referring now to FIGS. 1–10, there is shown, universal dental implant abutment system 100 for stably and rigidly securing a dental prosthesis to an implant body. Implant bodies, such as the implant body 90 shown in FIG. 1C are implanted into a patient's jawbone below the gum line. System 100 provides the connection interface between the prosthetic tooth or group of teeth to the implant body. A number of different methods are currently utilized to secure dental prostheses to implant bodies, each requiring different components. Universal dental implant abutment system 100 provides the advantage over prior art systems that its few components are adaptable for use in any one of the primary restorative methods being utilized at the present time. Additionally the abutment collar 110 of system 100 may serve as a tissue conditioning healing collar when combined with an appropriate cover screw, not shown. Thus, system 100 may be utilized for use in fixed cementable crown and bridge restorations, single tooth replacement, removable screw retained prosthetics as well as overdenture restorations.

Referring now to FIG. 1B, there is shown, universal dental implant abutment system 100 which includes an abutment collar 110 having a distal end 112 adapted for interconnection with an implant body. The proximal end of collar 110 is provided with a coronal cylindrical chimney 10 for coupling to the dental prosthesis. The dental prosthesis may be cast onto the coronal cylindrical chimney 10, adhesively bonded thereto, or where metallic prosthetic elements are utilized, may be joined by such methods as soldering, brazing, laser welding or other bonding techniques. The method used for securing the prosthesis to the coronal chimney 10 is not important to the inventive concepts being disclosed herein.

The abutment collar 110 is secured to the implant body by means of the fixation screw 120. Fixation screw 120 has a threaded distal end 15 which engages an internally threaded portion of the implant body. As will be described in following paragraphs, the distal end 112 of abutment collar 110 is particularly adapted to positionally locate the abutment collar in a particular position relative to the implant body and includes means for forming a rigid connection therewith. The fixation screw 120 includes a head portion 122 in which is formed an annular groove 20. An O-ring 130 is disposed within the groove 20 to provide a means for maintaining the fixation screw 120 within the longitudinal bore 13 of the abutment collar prior to assembly to an implant body. The O-ring 130 also aids in maintaining the axial alignment of screw 120 within bore 13, thereby facilitating the threaded engagement with the implant body 130. Further, the O-ring eliminates any potential for liquid migration into the implant and enhances the resistance of the screw to vibrationally induced loosening.

Referring now to FIG. 1C, there is shown, system 100 having a dental prosthesis 80 secured to the abutment collar 110. The distal end 112 of abutment collar 110 forms a hybrid male/female connection with the implant body 90, which connection will be further described in following paragraphs. The abutment collar 110 is fastened to the implant body 90 by means of the fixation screw 120, the threaded distal end 15 being threadedly engaged with a threaded bore 98 of the dental implant body 90. The dental implant body 90 includes a projecting portion 96, extending radially from a central projecting portion 95, which mates with an anti-rotation configuration formed in the distal end 112 of abutment collar 110, and will be further described in following paragraphs.

When a restoration method is to be utilized which employs a fastener for joining the prosthesis to the implant body, system 100 is easily adapted to accommodate that method of restoration. Abutment collar 110 is adapted to permit the dental professional to remove the coronal cylindrical chimney 10 from abutment collar 110 to expose the head portion 122 of the fixation screw 120, as shown in FIG. 1A. Fixation screw 120 is provided with a longitudinal bore 124 having a section 125 formed with internal threads 17. Thus, where a prosthesis is to be affixed to an implant body utilizing a fastener, such fastener engages the internal threads 17 of fixation screw 120.

Figure 2:
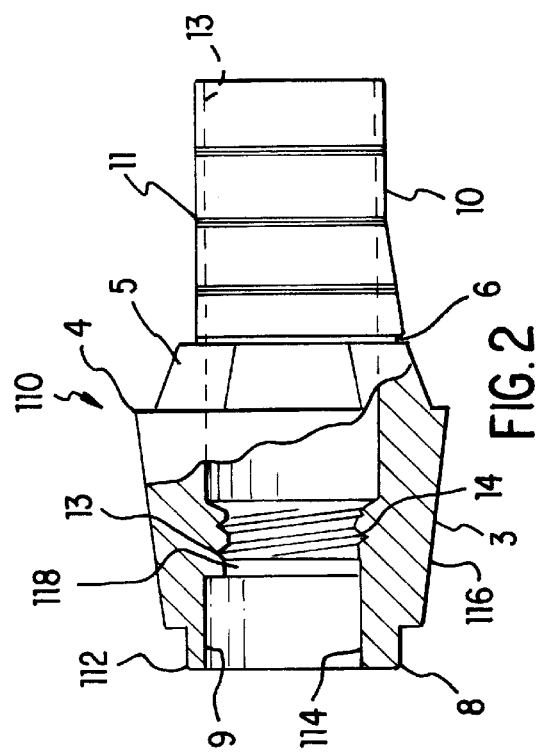
FIG. 2 is an elevation view, partially sectioned, of the abutment collar of the present invention.

Referring to FIG. 2, there is shown, abutment collar 110. Abutment collar 110 may be formed of a biocompatible metallic material composition. In one working embodiment, abutment collar 110 is formed of a titanium alloy, but may be formed of stainless steel, gold, or other materials approved by the FDA. The distal end 112 of abutment collar 110 is formed with a cylindrical extension 8 having an external taper configuration for securement to the proximal end of an implant body having a corresponding internal taper. Thus, a frictional fit between the cylindrical extension 8 of abutment collar 110 and an annular recess of the implant body provides a rigid connection therebetween, independent of the fixation screw. Obviously, the fixation screw provides the means by which the frictional fit between the cylindrical extension 8 and the corresponding annular opening 94, shown in FIG. 1C, of the implant body is achieved. The tapered cylindrical extension 8 defines a male plug which is received within the female socket portion 94 of an implant body 90. The distal end 114 of a through bore 13 which extends longitudinally through abutment collar 110 is provided with the means to prevent rotation of abutment collar 110 with respect to an implant body and provides the means by which the abutment collar can be positively positionally located (radially) with respect to the implant body in either a single location, keyway configuration shown in FIG. 2, or multiple positions polygonal configuration shown in both FIGS. 8 and 10.

Figure 3:
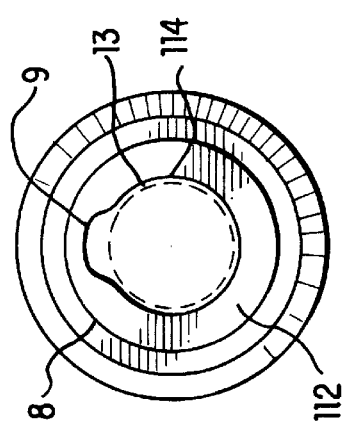
FIG. 3 is a distal end view of the abutment collar shown in FIG. 2.

Referring to FIG. 3, the distal end of the abutment collar is shown. The distal end 114 of the through bore 13 includes an anti-rotational recess configuration 9 formed therein. In the particular arrangement shown, the anti-rotational recess portion is in the form of a keyway, but other configurations may also be utilized, such as elliptical configurations or polygonal contours. As shown in FIG. 1C, the implant body 90 includes a centrally disposed projecting portion 95 having a cam-like projection or key 96 extending therefrom which is received within the keyway 9, locking the abutment collar against rotative displacement. Thus, the abutment collar 112 includes a male projecting portion formed by the tapered cylindrical extension 8 which is received within an annular recess 94 of the implant body. The abutment further includes a socket defined by the distal end 114 of through bore 13 for receiving the central projecting portion 95 of implant body 90, the recess having an internally tapered outer wall for frictional locking of the tapered extension 8 of abutment collar 110 therein. That arrangement provides a unique hybrid male/female connection between the abutment collar 110 and the implant body 90. The external surface of the tapered cylindrical extension 8 is formed with a Mores taper within the approximating range of 1°–2°, with a preferred taper being approximately 1°, 30'. The annular recess 94 of implant body 90 has a corresponding taper to provide the necessary frictional fit therebetween. The mating of the projection 96 with the keyway 9 provides a unidirectional orientation of the abutment collar with the implant body.

The proximal end of the abutment collar 110 is formed with a coronal cylindrical chimney 10 extending from the proximal end of a tapered hex portion 5. Indicia in the form of etched score lines 11 are disposed at 1 millimeter intervals along the length of cylindrical chimney 10. The distal end of the chimney 10, at its interface with the tapered hex portion 5 there is formed an annular groove 6. Annular groove 6 provides a reduced wall thickness area to facilitate accurate removal of the chimney portion for restoration methods utilizing a fastener to secure the prosthesis. The dental professional, either in the practitioner's office or laboratory, can easily mechanically remove the chimney portion 10 from the abutment collar 110 at the groove 6 using conventional tools found in the dental office or laboratory.

Upon removal of the coronal cylindrical chimney 10 from the abutment collar 112 what remains is a body portion 116 with a tapered hexagonal portion 5 at the proximal end thereof. Although the surface 5 is referred to as a tapered hex surface, the surface 5 may have any polygonal or non-circular contour which is tapered to allow for unirotational location (keyway configuration) or multi-location (polygonal configuration). The non-circular contour of the surface provides an anti-rotation feature for preventing rotation of the prosthetic device relative to the abutment collar. The surface is tapered within an approximating range of 35°–45° to provide for all mounting of prosthetics which may not be axially aligned with the longitudinal axis of the implant bodies that have been mounted within the jawbone of the patient. This is a particular problem which occurs where there are multiple implants to which a multi-unit bridge is to be secured. System 100 solves that problem by providing a tapered mating surface, surface 5, which permits the seating of prostheses which may be as much as 30° off axis and which otherwise would not properly seat on the abutment collar. The tapered surface 5 extends between a prosthesis seating surface 4 on the distal end of the tapered surface and the coronal cylindrical chimney 10 on the proximal end of the tapered surface. In the region between the tapered cylindrical extension 8 and the tapered surface 5, the external surface 3 of the abutment collar body 116 has a tapered emergence profile, providing a smooth transition between the external surface profile of the implant body, at the distal end, and the prosthesis disposed at the seating surface 4. The emergence profile provides for soft tissue compliance, allowing abutment collar 110 to be used as a tissue conditioner. When used as a tissue conditioner, the coronal chimney 10 is removed and an appropriate cover screw is engaged to the threads 17 of fixation screw 120, forming a closure for the proximal end of bore 13.

In an intermediate portion of the body portion 116 of abutment collar 110, within the through bore 13 there is a portion 118 having internal threads 14 formed therein. The threaded opening portion 118 of through bore 13 is dimensioned to permit the threaded portion 15 of fixation screw 120 to pass therethrough. The internal threads 14 are utilized by the dental professional when it is desired to separate the abutment collar 110 from the implant body 90 at some time subsequent to the abutment collar having been secured to the implant body. As previously discussed, the tapered extension 8 of the abutment collar is provided with a Mores taper, as is the internal mating surface of the implant body. Thus, once the fixation screw has been torqued down, the abutment collar cannot be separated from the implant body when the fixation screw has been removed, using finger pressure. The internal threads 14 of the abutment collar 110 permit a "jack screw" to be installed to force the separation of the abutment collar from the implant body, by application of a separation force therebetween.

Figure 4:
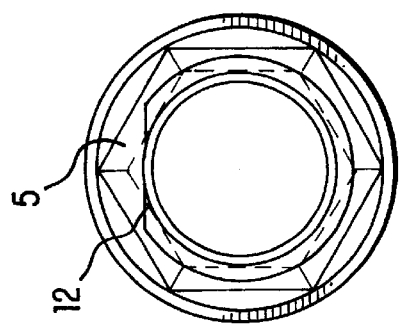
FIG. 4 is a proximal end view of the abutment collar shown in FIG. 2.

The implant body 90 is disposed beneath the gum line of a patient, with the abutment collar 110 disposed in the tissue portion thereof. Where the abutment collar 110 utilizes an anti-rotation feature 9 which mates with the implant body in a single orientation, it is important that the dental professional have some means for identifying the location of the keyway relative to the external surface of the abutment collar. As shown in FIG. 4, the coronal cylindrical chimney 10 is formed with a flat surface 12 formed on one side thereof. Flat surface 12 is disposed in radial alignment, relative to a longitudinal axis of the abutment collar 110, with the keyway 9. Thus, the dental professional can be assured of a proper orientation of the abutment collar with respect to the implant body by maintaining alignment between the flat surface 12 and the key 96 of the implant body.

Figure 6:
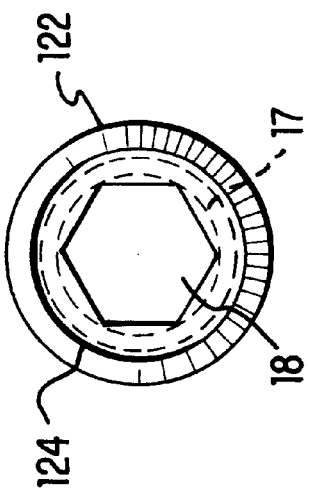
FIG. 6 is a proximal end view of the fixation screw shown in FIG. 5.
Figure 5:
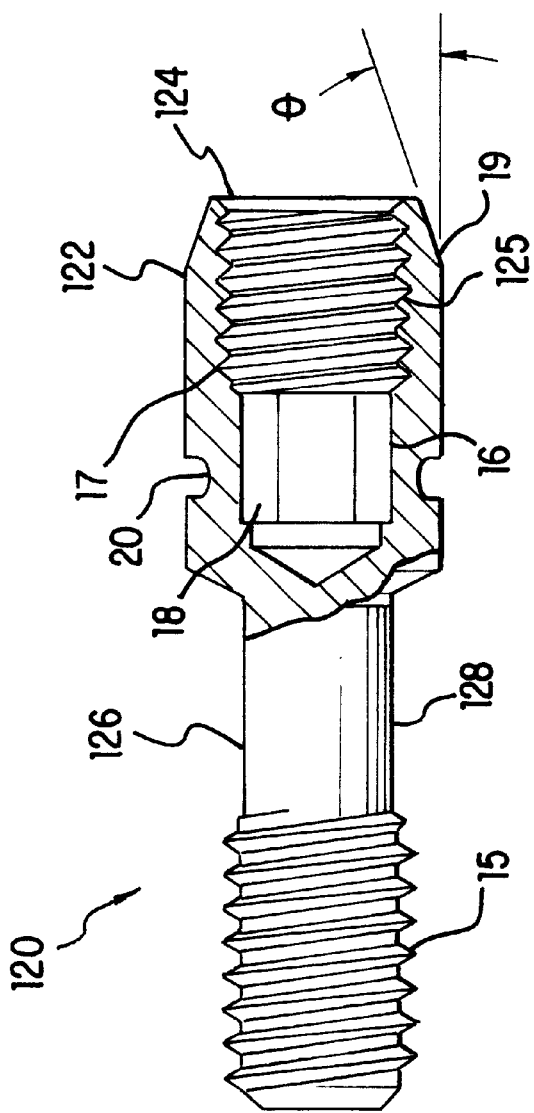
FIG. 5 is an elevation view, partially sectioned, of the fixation screw of the present invention.

Turning now to FIGS. 5 and 6, there is shown the fixation screw 120 of universal dental implant abutment system 100. Fixation screw 120 is formed of a biocompatible metallic material composition. In one working embodiment, fixation screw 120 is formed of a titanium alloy. As previously discussed, the distal end of fixation screw 120 includes a shank 126 having threads 15 formed on a distal end portion thereof. Between the threaded portion of the shank and the head portion 122, the shank 126 has an unthreaded portion 128 which is disposed in the internally threaded portion 118 of abutment collar 110, when assembled therewith. Adjacent the distal end of the head portion 122, an annular groove 20 is formed in the external surface thereof. As previously discussed, annular groove 20 provides a seating surface for an O-ring which provides a fluid seal within the through bore 13 of abutment collar 110. Further, the O-ring disposed in annular groove 20 acts as a retention device to maintain the fixation screw 120 within the through bore 13 of abutment collar 110 prior to assembly to the implant body and also serves to maintain the fixation screw in axial alignment with the through bore 13.

Of particular importance, is the structure of the head portion 122 of fixation screw 120. The proximal end of the fixation screw 120 has a bore 124 extending longitudinally therein. Bore 124 is open on the proximal end and is formed by two distinct longitudinally spaced sections 16 and 125. Section 16 is defined by an internal surface configuration having a non-circular cross-sectional contour for accepting a driving tool therein. While a polygonal contour is shown in the drawings, it should be understood that any non-circular contour capable of being bidirectionally torqued could be utilized in system 100 without departing from the inventive concept thereof. Thus, the internal polygonal surface contour 18 disposed within a bore 124 is mated with a polygonal seating tool for rotating the fixation screw 120 to engage threads 15 with the threaded aperture 98 of implant body 90. The section 125 of bore 124 is formed with internal threads 17 which are sized to be threadedly engaged by a screw utilized to retain a prosthesis or a cover screw, when the coronal cylindrical chimney 10 is removed from the abutment collar 110. While the threaded section 125 is shown to be disposed adjacent the coronal end of the bore 124, and the polygonally contoured section 16 is shown disposed distal thereto, the location of those sections may be interchanged. The threaded portion 125 may be disposed at the distal end of bore 124, and a polygonal section located at the distal end of the bore, with the polygonal opening being dimensioned to permit the prosthesis fastener to pass therethrough.

The external surface of head 122 has a frustro-conical surface portion 19 adjacent the proximal end thereof. The portion 19 is tapered at an angle θ. Angle θ is in the approximating range of 17°–19°. This taper also minimizes draw of the prosthesis, allowing coupling with a prosthesis that is not in axial alignment with the axis implant body.

Figure 7:
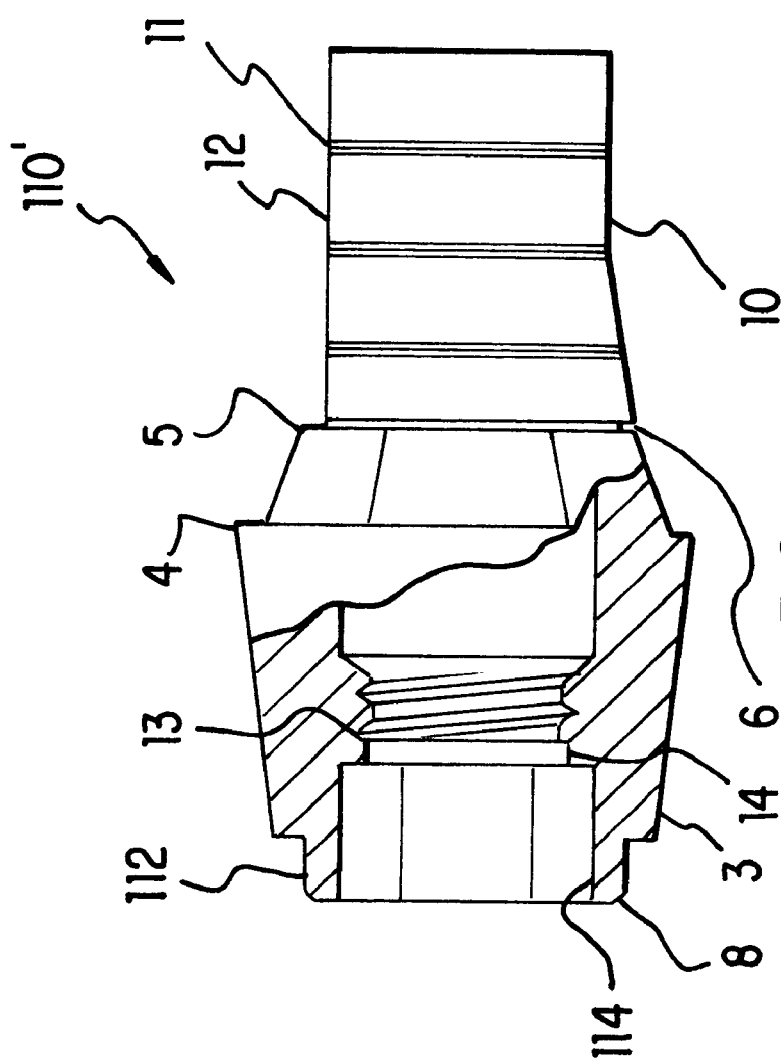
FIG. 7 is an elevation view, partially sectioned, of another configuration of the abutment collar of the present invention.
Figure 8:
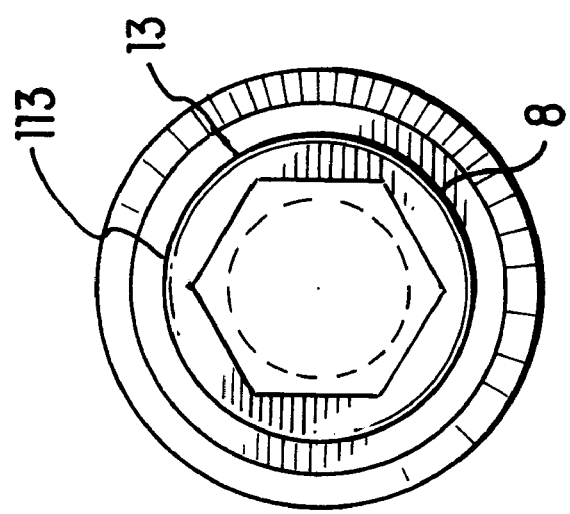
FIG. 8 is a distal end view of the abutment collar shown in FIG. 7.

Referring now to FIGS. 7 and 8, there is shown, an alternate configuration of the abutment collar of system 100. Abutment collar 110' differs from abutment collar 110 in its configuration of the hybrid male/female connection arrangement at the distal end 112. Instead of a keyway formed in the opening portion of distal end 114, abutment collar 110' has an internal surface contour 113 having a hexagonal cross-sectional configuration. The hexagonal surface contour of the opening provides an anti-rotational function, as previously discussed. The distal end 112 is still provided with the male coupling portion formed by the tapered cylindrical extension 8 and the hexagonally contoured opening 113 mates with a similarly shaped projecting portion 95 of the implant body 90, with the portion 96 being eliminated from the structure shown in FIG. 1C.

Figure 9:
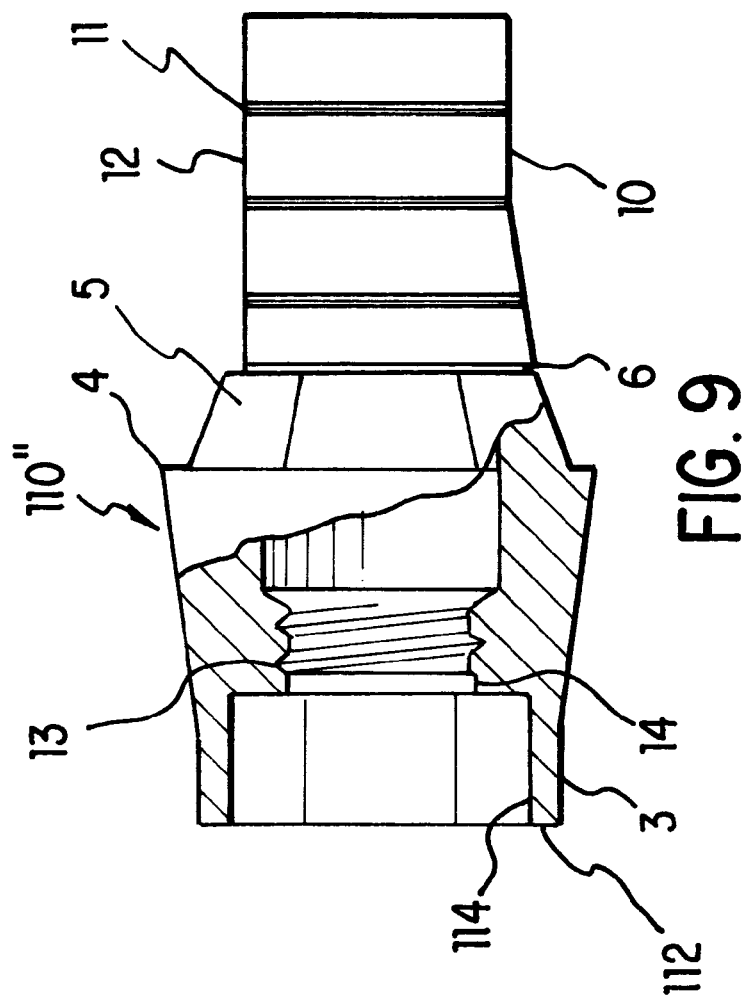
FIG. 9 is an elevation view, partially sectioned, of another configuration of an abutment collar of the present invention; and, FIG. 10 is a distal end view of the abutment collar shown in FIG. 9.
Figure 10:
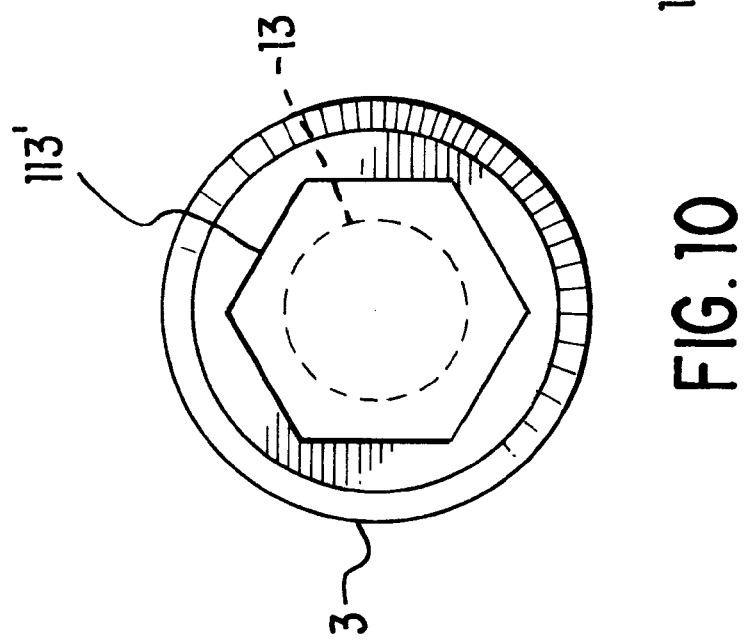

Referring now to FIGS. 9 and 10, there is shown yet another configuration of the abutment collar of system 100. Abutment collar 110" provides a female coupling for mating with an implant body having only a male coupling structure, that structure not being designed to utilize the unique hybrid male/female connection previously described. The distal portion 114 of through bore 13 is provided with an internal surface contour 113' which provides an anti-rotation function. The internal surface contour 113 is non-circular so as to prevent relative rotation between the abutment collar and the implant body. In the particular configuration shown, a polygonal contour 113' is formed within the distal end 114 of through bore 13. In this arrangement, the external surface of the distal end 112 of abutment collar 110" is not tapered and the fixation screw 120 is the only means of securement between the abutment collar and the implant body. In this configuration, although the connection of the abutment collar 110" with an implant body is not as rigid and stable as that achieved with the hybrid male/female connection, the internal polygonal surface contour 113' which mates with a corresponding polygonal protrusion 95 of implant body 90 provides resistance to rotation of the abutment collar relative to the implant body, and provides distinct orientation reference positions for locating the abutment collar relative to the implant body. Obviously, the number of polygonal surfaces determines the number of distinct positions in which the abutment collar may be located relative to the implant body and the flat surface portion 12 of the coronal cylindrical chimney 10 provides an orientation reference for the dental professional when performing a restoration in a patient's mouth.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A universal dental implant abutment system for securement to an implant body, comprising:

an abutment collar having a bore extending longitudinally therethrough said abutment collar having a proximal end portion adapted for fixation of a dental prosthesis thereto, said proximal end portion adapted for fixation being removable for attachment of a prosthesis by a fastener to a fixation screw located in the bore, said abutment collar having a distal end portion having an extension sized for frictional fit within a matching portion of an implant body and a recessed area for receiving, for a frictional fit, a matching extension on the implant body; and, the fixation screw disposed within said longitudinal bore of said abutment collar having a threaded distal end for threaded engagement with the implant body and a head portion formed on a proximal end of the fixation screw, said head portion having a longitudinally directed bore open on said proximal end of the fixation screw and having first and second longitudinally spaced sections formed within said bore of said head portion, said first section having a non-circular cross sectional contour adapted to receive a driving tool therein, said second section having internal threads formed therein for threaded engagement with a retention fastener of a prosthesis.

2. The universal dental implant abutment system of claim 1 wherein the bore extending longitudinally through the abutment collar includes a threaded wall portion which, in cooperation with a jack screw inserted therein, functions to disconnect the frictional fit between the abutment collar and the implant body.

3. A universal implant abutment system comprising, in combination:
a universal prosthetic abutment means, anti-rotational means for providing a rigid and stable connection between said universal prosthetic abutment means and an implant body, and a fixation screw having an axial bore in the proximal portion thereof, said fixation screw having an externally threaded distal portion for attachment to the implant body and mounting of the universal prosthetic abutment means to said implant body, said universal prosthetic abutment means having integral prosthesis attachment means thereon and said fixation screw having prosthesis attachment means therein for alternatively attaching a prosthesis, the fixation screw prosthesis attachment means comprising a section within the bore of the fixation screw having internal threads therein for threaded engagement with a retention fastener of the prosthesis.

4. The universal abutment system of claim 3 wherein said fixation screw further includes, within the bore, noncircular means for receiving a like shaped engaging tool.

5. The universal abutment system of claim 3, wherein said abutment collar has a distal end adapted to positionally align in a desired orientation the abutment collar on the implant body.

6. The universal abutment system of claim 3, wherein said fixation screw includes an upper portion having an annular groove in an external surface thereof and means located in said annular collar for maintaining the axial alignment of said fixation screw within the longitudinal bore of said abutment collar prior to assembly to an implant body.

7. The universal abutment system of claim 6 wherein said means for maintaining the axial alignment of said fixation screw within the longitudinal bore of said abutment collar prior to assembly to an implant body is an o-ring disposed within said annular groove.

8. The universal abutment system of claim 3, wherein said anti-rotational means further comprises a hybrid male/female connection on the abutment collar.

9. The universal abutment system of claim 8, wherein said hybrid male/female connection includes an elongate means for insertion into a well on the proximal end of the implant body and a well means for receiving an elongate means on the proximal end of the implant body.

10. The universal abutment system of claim 9, wherein said elongate means includes a portion projecting radially from a central portion of said dental implant body said radially projecting portion mating with said anti-rotational means, a threaded distal end of said fixation screw being engaged with a threaded bore in said dental implant body, and said internally threaded fixation screw having a longitudinally directed bore with a first section having a noncircular cross sectional contour adapted to receive a driving tool and a second section having an internally threaded surface for engagement with a male threaded fastener functioning to attach a prosthetic thereto.

11. The universal abutment system of claim 3, wherein said abutment means further includes a removable cylindrical coronal chimney disposed upon the proximal end of said abutment means and the longitudinal bore of said fixation screw has a threaded surface, the removable cylindrical coronal chimney and the threaded surface of the bore in the fixation screw functioning to alternatively receive a dental prosthesis.

12. The universal abutment system of claim 3 further including tool engaging means within the bore of the fixation screw for receiving a driving tool.

13. The universal abutment system of claim 3 wherein said abutment collar is formed from a biocompatible composition selected from the group consisting of titanium alloy, stainless steel, gold, metallic and ceramic compositions.

14. The universal implant abutment system of claim 3 wherein the prosthesis is attached to the integral prosthesis attachment means on the universal prosthetic abutment means by casting of the prosthesis thereon, adhesively bonding the prosthesis thereto or by soldering, brazing or laser welding of metallic elements of the prosthesis thereto.

15. An implant abutment system for securing a prosthesis to a bone, comprising:
an implant body implantable in a bone, said implant body including a reception end portion having coaxially disposed internal threads;
an abutment collar including a proximal end portion adapted to receive the prosthesis and a distal end portion engageable with said implant body, said abutment collar having a axial, longitudinal bore extending therethrough;
a fixation screw receivable in said longitudinal bore through a proximal opening in said abutment collar, said fixation screw including a threaded distal end portion engageable with said coaxially disposed internal threads of said implant body when received in said longitudinal bore, the bore of said fixation screw further including a section having internal threads therein for threaded engagement with a retention fastener of the prosthesis; and
tapered means on said abutment collar proximal end and said implant body reception end providing frictional engagement between said abutment collar and said implant body.

16. The implant abutment system of claim 15 further including positioning means located between adjacent surfaces of the fixation screw and the abutment collar for axially aligning said abutment collar and said fixation screw relative to the implant body in the bone of a patient.

17. The implant abutment system of claim 16 wherein the positioning means comprises a circumferential notch within the exterior surface of the fixation screw and a o-ring disposed in said notch and in circumferential contact with the surface of the bore in said abutment collar.

18. An implant abutment system for securing a prosthesis to a bone, comprising:
an implant body implantable in a bone said implant body including a reception end portion having coaxially disposed internal threads;
an abutment collar including a proximal opening for receiving a fixation screw and a distal end portion engageable with said implant body, said abutment collar having a longitudinal bore extending from the proximal end to the distal end, a fixation screw receivable in said longitudinal bore through the proximal opening in said abutment collar, said fixation screw including an externally threaded distal end portion engageable with said coaxially disposed internal threads of said implant body when received in said longitudinal bore; and a means for frictional attachment of said abutment collar to said implant body wherein a portion of the implant body is inserted into an opening in the abutment collar and an extension portion of the abutment collar is inserted into an opening in the implant body.

19. An implant abutment system for securing a prosthesis to a bone, comprising:

an implant body implantable in a bone said implant body including a reception end portion having coaxially disposed internal threads;

an abutment collar including a proximal end portion for fixably receiving a prosthesis and a distal end portion engageable with said implant body, said abutment collar having a longitudinal bore extending therethrough;

a fixation screw receivable in said longitudinal bore of said abutment collar, through a proximal opening thereof, said fixation screw including a threaded distal end portion engageable with said coaxially disposed internal threads of said implant body when received in said longitudinal bore; and means for frictional attachment of said abutment collar to said implant body wherein a portion of the implant body is inserted into a like-sized opening in the abutment collar and an extension portion of the abutment collar is inserted in to a like-sized opening in the implant body.

20. The universal implant abutment system of claim 19 wherein the proximal end portion of the abutment collar for receiving a prosthesis comprises a coronal chimney integral therewith.

21. The universal implant abutment system of claim 20 wherein the coronal chimney rests on an external tapered hex portion of the proximal end of the abutment collar.

22. An implant abutment system for securing a dental prosthesis to a jawbone, comprising:

an implant body implantable in the jawbone below a gumline, said implant body including a reception end portion having coaxially disposed internal threads; an abutment collar including a proximal end portion for fixably receiving the dental prosthesis and a distal end portion frictionally engageable with said implant body, said abutment collar having a longitudinal bore extending therethrough, the abutment collar adapted to reside within the gum line with at least a part of the proximal end portion extending above the gum line;

a fixation screw receivable in said longitudinal bore through a proximal opening therein, said fixation screw including a threaded distal end portion engageable with said coaxially disposed internal threads of said implant body when received in said longitudinal bore; and means for preventing rotation between said abutment collar and said implant body.

* * * * *